(12) United States Patent
O'Brien et al.

(10) Patent No.: US 10,216,908 B2
(45) Date of Patent: Feb. 26, 2019

(54) MEDICATION ASSURANCE SYSTEM AND METHOD

(71) Applicant: Viavi Solutions Inc., Milpitas, CA (US)

(72) Inventors: Nada A. O'Brien, Santa Rosa, CA (US); Christopher G. Pederson, Santa Rosa, CA (US)

(73) Assignee: VIAVI Solutions Inc., San Jose, CA (US)

( * ) Notice: Subject to any disclaimer, the term of this patent is extended or adjusted under 35 U.S.C. 154(b) by 0 days.

(21) Appl. No.: 15/600,844

(22) Filed: May 22, 2017

(65) Prior Publication Data

US 2017/0262615 A1    Sep. 14, 2017

Related U.S. Application Data

(63) Continuation of application No. 14/280,468, filed on May 16, 2014, now Pat. No. 9,665,689.
(Continued)

(51) Int. Cl.
| | |
|---|---|
| *G01J 3/28* | (2006.01) |
| *G06F 19/00* | (2018.01) |
| *A61J 7/00* | (2006.01) |
| *A61J 7/04* | (2006.01) |
| *G04C 21/16* | (2006.01) |

(52) U.S. Cl.
CPC ........ *G06F 19/3462* (2013.01); *A61J 7/0076* (2013.01); *A61J 7/04* (2013.01); *G01J 3/2803* (2013.01); *G04C 21/16* (2013.01); *G06F 19/00* (2013.01)

(58) Field of Classification Search
CPC .... G06F 19/3462; G16H 20/13; G16H 20/60; G16H 20/70; G16H 20/90; A61J 7/04
See application file for complete search history.

(56) References Cited

U.S. PATENT DOCUMENTS

| 6,663,846 B1 | 12/2003 | McCombs et al. |
| 7,154,102 B2 | 12/2006 | Poteet et al. |
| (Continued) | | |

FOREIGN PATENT DOCUMENTS

| WO | WO 2004/109262 | 12/2004 |
| WO | WO 2011/112606 | 9/2011 |

OTHER PUBLICATIONS

O'Brien et al., "Miniature near-infrared (NIR) spectrometer engine for handheld applications", Next-Generation Spectroscopic Technology V, SPIE, vol. 8374, No. 1, May 11, 2012, 8 pages, XP060003026.
(Continued)

*Primary Examiner* — Yara B Green
(74) *Attorney, Agent, or Firm* — Harrity & Harrity, LLP

(57) ABSTRACT

A medication assurance system for verification of both the medication and the patient is disclosed. A portable spectrometer is used to obtain a light spectrum of the medication. A subject identification or biometric device is used to identify the patient. A controller coupled to the portable spectrometer and the subject identification device identifies the medication by performing a chemometric analysis of the light spectrum. Based on the medication identified and the patient identified, the controller can determine if the medication is to be taken by the patient.

20 Claims, 10 Drawing Sheets

Related U.S. Application Data

(60) Provisional application No. 61/824,925, filed on May 17, 2013.

(56) References Cited

U.S. PATENT DOCUMENTS

| | | | |
|---|---|---|---|
| 7,359,765 B2 | 4/2008 | Varvarelis | |
| 7,570,786 B2 | 8/2009 | Ateya | |
| 7,796,043 B2 | 9/2010 | Euliano et al. | |
| 8,805,577 B2 | 8/2014 | Buisman | |
| 9,251,493 B2* | 2/2016 | Jacobs | A61J 7/04 |
| 9,665,689 B2 | 5/2017 | O'Brien | |
| 2002/0113210 A1* | 8/2002 | Treado | G01J 3/2823 250/331 |
| 2003/0204330 A1 | 10/2003 | Allgeyer | |
| 2004/0081587 A1 | 4/2004 | Melker et al. | |
| 2005/0077476 A1* | 4/2005 | Poteet | G01N 21/64 250/461.1 |
| 2006/0062734 A1* | 3/2006 | Melker | G06F 19/3418 424/10.1 |
| 2007/0123772 A1 | 5/2007 | Euliano et al. | |
| 2007/0224128 A1 | 9/2007 | Dennis et al. | |
| 2008/0133265 A1 | 6/2008 | Silkaitis | |
| 2008/0228428 A1 | 9/2008 | Balss | |
| 2009/0127339 A1 | 5/2009 | Needhan | |
| 2009/0143900 A1 | 6/2009 | Hyde | |
| 2009/0144190 A1 | 6/2009 | Hyde et al. | |
| 2010/0045978 A1 | 2/2010 | Potuluri et al. | |
| 2010/0131097 A1* | 5/2010 | Young | G01N 21/31 700/244 |
| 2010/0232640 A1 | 9/2010 | Friend | |
| 2010/0255598 A1 | 10/2010 | Melker et al. | |
| 2011/0275683 A1 | 11/2011 | Graul | |
| 2012/0212735 A1 | 8/2012 | Palmskog et al. | |
| 2012/0330684 A1 | 12/2012 | Jacobs | |
| 2013/0142406 A1 | 6/2013 | Lang | |
| 2013/0221082 A1 | 8/2013 | Botten | |
| 2013/0256534 A1 | 10/2013 | Micheels et al. | |
| 2013/0256568 A1 | 10/2013 | Endo et al. | |
| 2013/0279774 A1 | 10/2013 | Helgason | |
| 2014/0131578 A1 | 5/2014 | Hruska | |

OTHER PUBLICATIONS

Extended European Search Report corresponding to EP 14168795.4, dated Feb. 23, 2015, 10 pages.

Medfollo Pillbox, "Welcome to MedFollo", http://www.medfollopillbox.com/, Apr. 30, 2014, 3 pages.

Vermeire et al., "Patient adherence to treatment: three decades of research", A comprehensive review, Journal of clinical pharmacy and therapeutics, 26(5), 2001, pp. 331-342.

Medco Health Solutions, Inc., http://www.prnewswire.com/news-releases/new-study-finds-lack-of-medicine-compliance-leads-to-high-medical-costs-67061882.html, 2005, 5 pages.

* cited by examiner

MEDICATION ASSURANCE SYSTEM AND METHOD

CROSS-REFERENCE TO RELATED APPLICATIONS

This application is a continuation of U.S. patent application Ser. No. 14/280,468, filed May 16, 2014 (now U.S. Pat. No. 9,665,689), which claims priority from U.S. Provisional Patent Application No. 61/824,925, filed May 17, 2013, the disclosures of which are incorporated herein by reference.

TECHNICAL FIELD

The present invention relates to medical equipment and methods, and in particular to equipment and methods for drug verification and medication assurance.

BACKGROUND OF THE INVENTION

Non-adherence to medication schedules causes $300 billion annual cost to healthcare system in the US, including 10% of hospital admissions and 23% of nursing home admissions. Globally, non-adherence claims millions of lives and poses threat of untreatable diseases (Vermeire, E., Hearnshaw, H., Van Royen, P., & Denekens, J. (2001). *Patient adherence to treatment: three decades of research. A comprehensive review. Journal of Clinical Pharmacy and Therapeutics*, 26(5), 331-342). For diabetes, for every $1 spent on medication, $7 is saved on other medical costs such as hospitalization. For high cholesterol, for every $1 spent, $5.10 is saved. For hypertension, for every $1 spent, $3.98 is saved (Medco Health Solutions, 2005).

Another example is tuberculosis, which results in 1.9 million lethal outcomes each year. Tuberculosis is normally curable with antibiotic medication administered over a period of 6 months. Adherence to tuberculosis medication saves lives and prevents spread of drug-resistant tuberculosis strains. However, ensuring medical adherence can be difficult in developing countries, especially in remote areas. Lack of adherence can result in death and development of drug-resistant forms of tuberculosis, which can infect other people and impede containment of the disease.

From the medication adherence perspective, three conditions must be ensured: 1) an appropriate medicine must be administered 2) at an appropriate time or time intervals 3) to a right person or persons. The medication assurance systems of the prior art can be broken down into three general categories: A) electronic pillboxes; B) software-based products; and 3) pill identification systems. The latter systems are mostly used for a specific task of drug identification for dispensing and marking.

Electronic pillboxes, or "smart" pillboxes, address the conditions 1) and 2) above, that is, taking the right medicine at the right time. By way of example, MedFolio™ pillbox, distributed online at www.medfoliopillbox.com, is an electronic pillbox serving as a medication identifier and reminder system. MedFolio pillbox connects to a personal computer. A software program running on the personal computer allows the patient or the caregiver to easily customize the device to specific medication regimens. Med-Folio pillbox has a series of medication reminders, such as audio alerts and visual lighting alerts. The software program can communicate with a secure website to offer the option of receiving electronic messaging reminders.

Another example is MedReady™ cartwheel pillbox pre-loadable with pills, manufactured and distributed by MedReady, Inc., of Burlingame, Calif., USA. The MedReady cartwheel pillbox sounds an alarm, prompting the user to take pills at regular time intervals. A battery back-up is provided for preventing medication interruptions caused by power outages.

Yet another example of an electronic pillbox is MedSignals™ pillbox, manufactured by MedSignals, San Antonio, Tex., USA. The MedSignals pillbox reminds the patient, via alarms and a textual display, when and how to take the medications, monitors the time of administering the medications, and communicates the collected information to remote care managers. Furthermore, yet another example is a Medminder™ electronic pillbox, manufactured by Med-Minder Inc., Needham, Mass., USA. Once set up, the Medminer pillbox provides patient reminders and remote medication adherence capabilities. The Medminder pillbox reminds the patient to take a medicine by lighting up an appropriate compartment. If a cup of the compartment is not lifted within an assigned time, the patient gets auditory prompts, as well as optional phone calls, text messages, and emails. A remotely located caregiver can assess the medication adherence information via the Internet.

An example of a software-based medication assurance system is a Pill Jogger™ smartphone app, developed by Pill Jogger Inc., San Francisco, Calif., USA. The Pill Jogger app reminds patients to take their pills, and keeps track of the pills taken.

A "medical substance recognition system" is disclosed by Peter Botten in US Patent Application Publication 2013/0221082 A1. The system controls pill dispensing to prevent dispensing errors. The system includes a "recognition device" based on a machine-vision digital camera, which recognizes various pills by their visual appearance. Botten also teaches that the pill recognition device can utilize "the physical, chemical, luminescent and possibly other features" of the pills.

Wade M. Poteet et al. in U.S. Pat. No. 7,154,102 B2 disclose a system and methods for detection and identification of chemical substances using UV fluorescence spectroscopy. Pharmaceuticals can be detected and identified from wavelengths of UV fluorescence spectral peaks, and concentrations of the pharmaceuticals can be evaluated from the strength of the UV fluorescence signal.

Prasant Potuluri et al. in US Patent Application Publication 2010/0045978 A1 disclose a system using a "spectral signature" of a medication for verification and identification purposes. The data processing includes correction for "response function of the spectrometer", intensity normalization, fluorescence removal, extracting the spectral signature, and comparing the spectral signature to a database of spectral signatures of known pharmaceuticals.

Richard Garfein from University of San Diego, La Jolla, Calif., USA, has suggested to provide via Internet cell phone video recordings of patients taking tuberculosis medicine at their homes, as a proof of adherence to antibiotic treatment. This method has been termed "VCP-DOT", or Video Cell Phone Directly Observed Therapy. However, VCP-DOT does not allow a medical professional to verify that a correct antibiotic medication was taken by the patient.

The prior art lacks a medication assurance system that would verify both the medication to be taken and the patient identity, reducing chances of incorrect medication, while providing an objective evidence of the fact of taking an appropriate medication by an appropriate person at appropriate time.

SUMMARY OF THE INVENTION

A medication assurance system of the invention includes means for objective verification of both the medication and the patient. Preferably, a handheld near-infrared (NIR) spectrometer based on a laterally variable filter (LVF) is used to identify the medication, and a biometric device, such as a fingerprint scanner, is used to identify the patient. Both identifications can be performed as a matter of seconds, providing quick, simple, and convenient medication verification and assurance.

In accordance with the invention, there is provided a medication assurance system comprising:

a portable spectrometer for obtaining a light spectrum of a medication;

a subject identification device for identifying a subject of medication; and a controller coupled to the portable spectrometer and the subject identification device, configured for identifying the medication from the light spectrum obtained by the portable spectrometer using a chemometric analysis; and determining if the medication is to be taken by the subject.

In accordance with the invention, there is further provided a medication assurance system comprising:

a portable spectrometer for obtaining a light spectrum of a medication;

a subject identification device for identifying a subject of medication; and a controller coupled to the portable spectrometer and the subject identification device, configured for identifying the medication from the light spectrum obtained by the portable spectrometer using a chemometric analysis, and providing a record of administering the identified medication to the identified subject, or person.

In a preferred embodiment, the portable spectrometer includes a light source for illuminating the medication, a medication holder for holding the medication being illuminated, a laterally variable optical filter (LVF) for receiving light reflected from, or transmitted through the medication, and a photodetector array optically coupled to the LVF for wavelength-selective detection of the reflected or transmitted light, respectively.

In accordance with the invention, there is further provided a method for preventing a subject from taking an incorrect medication, the method comprising:

(a) using a portable spectrometer to obtain a light spectrum of a medication;

(b) identifying the medication by performing a chemometric analysis of the light spectrum obtained in step (a);

(c) identifying the subject using a biometric device;

(d) for the subject identified in step (c), determining an associated medication based on a pre-existing record;

(e) determining that the medication identified in step (b) is not the associated medication determined in step (d); and (f) upon completion of step (e), generating an alarm for informing the subject that the medication is an incorrect medication.

In accordance with another aspect of the invention, there is further provided a method for tracking administering of a mediation to a subject, the method comprising:

(a) using a portable spectrometer to obtain a light spectrum of a medication;

(b) identifying the medication by performing a chemometric analysis of the light spectrum obtained in step (a);

(c) identifying the subject using a biometric device;

(d1) creating a record including: a timestamp; the medication identified in step (b); and the subject identified in step (c).

BRIEF DESCRIPTION OF THE DRAWINGS

Exemplary embodiments will now be described in conjunction with the drawings, in which.

DETAILED DESCRIPTION OF THE INVENTION

While the present teachings are described in conjunction with various embodiments and examples, it is not intended that the present teachings be limited to such embodiments. On the contrary, the present teachings encompass various alternatives and equivalents, as will be appreciated by those of skill in the art.

Figure 1:
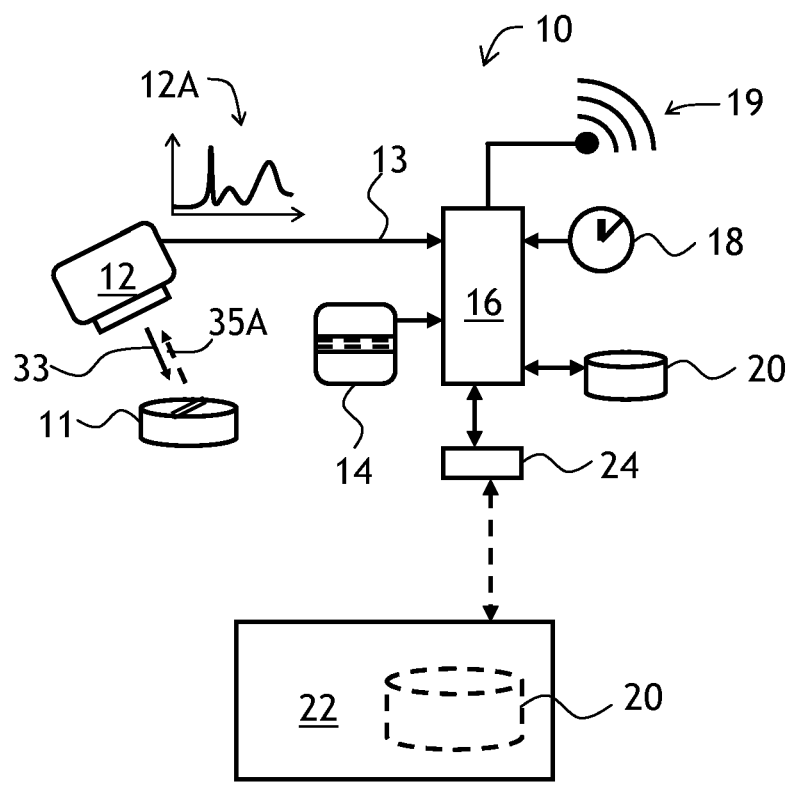
FIG. 1 is a block diagram of a medication assurance system of the invention.

Referring to FIG. 1, a medication assurance system 10 of the invention includes a portable near infrared (NIR) reflection spectrometer 12 for obtaining a diffuse reflection spectrum 12A of a pill 11. A fingerprint reader 14 is used for identifying a patient, not shown. A controller 16 is coupled to the portable NIR reflection spectrometer 12 and the fingerprint reader 14. The controller 16 is configured for identifying the pill 11 by performing a chemometric analysis of the diffuse reflection spectrum 12A obtained by the portable spectrometer 12, and for identifying the patient based on a fingerprint image provided by the fingerprint reader 14. The controller 16 is configured for determining if the identified pill 11 is to be taken by the identified patient, and can also be configured for providing a record of administering the identified pill 11 to the identified patient.

In the embodiment shown, the medication assurance system 10 includes a clock 18 coupled to the controller 16. A storage device 20 can be coupled to the controller 16 for storing a record comprising an identifier of the patient; an identifier of the pill 11; and a timestamp including the time of administering the pill 11 to the patient. While the scheduled pill 11 administering time can be stored in the controller's 16 memory, the actual time the pill 11 was taken can be provided by the clock 18. The stored records can be used to verify that the pill 11 has indeed been administered to the patient, thus establishing a medication record. When the medication assurance system 10 is used for clinical trials of a new drug, accumulated medication records allow the clinical trial personnel to verify adherence to the medication schedule, thus substantiating the clinical trial findings about efficacy of the new drug.

The storage device 20 can be optionally disposed at a remote location 22, and the medication assurance system 10 can include a wireless transmitter 24 for transmitting the medication record to the remote location 22 for storage on the remote storage device 20. This allows one to centralize storage of multiple record from multiple medication assurance systems 10, e.g. disposed at patient's homes or caregiver's locations, at the single remote location 22.

Figure 2:
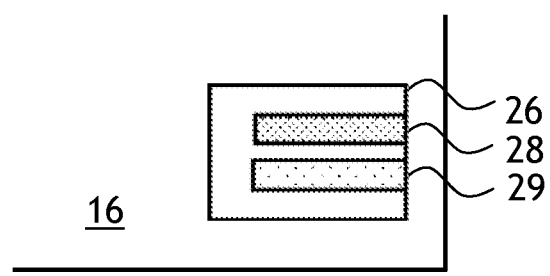
FIG. 2 is a schematic view of a memory unit of the system of FIG. 1.

Referring to FIG. 2 with further reference to FIG. 1, the controller 16 can include a non-transitional memory 26 for storing a time schedule of administering of the medication to the patient, or in other words a medication schedule 28. The non-transitional memory 26 can also store patient/medication information 29 in form of patient ID e.g. patient name, admission number, and fingerprint samples, and medications associated with the patient as identified by the fingerprint samples. In this embodiment, the medication assurance system 10 of FIG. 1 includes an alarm device 19 e.g. an audible or a visual alarm, coupled to the controller 16. The alarm device 19 can provide an audible or visible warning signal when the patient identified using the fingerprint reader 14 is going to take the pill 11 identified by the controller 16 to be different from the associated medication. In addition, the controller 16 can be configured to cause the alarm device 19 to provide an audible or visible reminder of one of the times for the patient to take the associated medication.

The alarm, clock, remote storage, and other functions can be conveniently implemented using computational and communication capabilities of smartphones. In a smartphone implementation, all of the functions of the controller 16 can be performed by the smartphone's microprocessor. The smartphone can be connected to the portable NIR reflection spectrometer 12 via a link 13 (FIG. 1), for example a USB cable, or a standardized wireless link such as Bluetooth™. The function of the transmitter 24 would be performed by the smartphone's wireless data carrying capability. Furthermore, many smartphones nowadays include a global positioning system (GPS). Thus, the medication record provided by a smartphone-enabled medication assurance system can include not only time, but also a GPS location where the known or verified medication has been administered to a known or verified subject, or person.

The fingerprint reader 14 can be replaced with another biometric device such as an eye iris scanner, or more generally another subject identification device, for example a digital camera equipped with facial recognition software. The portable NIR reflection spectrometer 12 can be replaced with a portable reflection, transmission, or transflection spectrometer operating in infrared, visible, or ultraviolet parts of the light spectrum. Transmission spectrometers can be used for transparent medications e.g. liquid medicines or mixtures. Transflection spectrometer geometries can be used for translucent samples or powders. In a transflection measurement, the collected light includes reflected light, as well as light transmitted through the sample and reflected to propagate again through the sample. The collected light can include light diffusely reflected from both the top and the bottom surfaces of the sample. A transflection spectrum measurement configuration will be considered further below, after reflective and transmissive configurations.

Figure 3A:
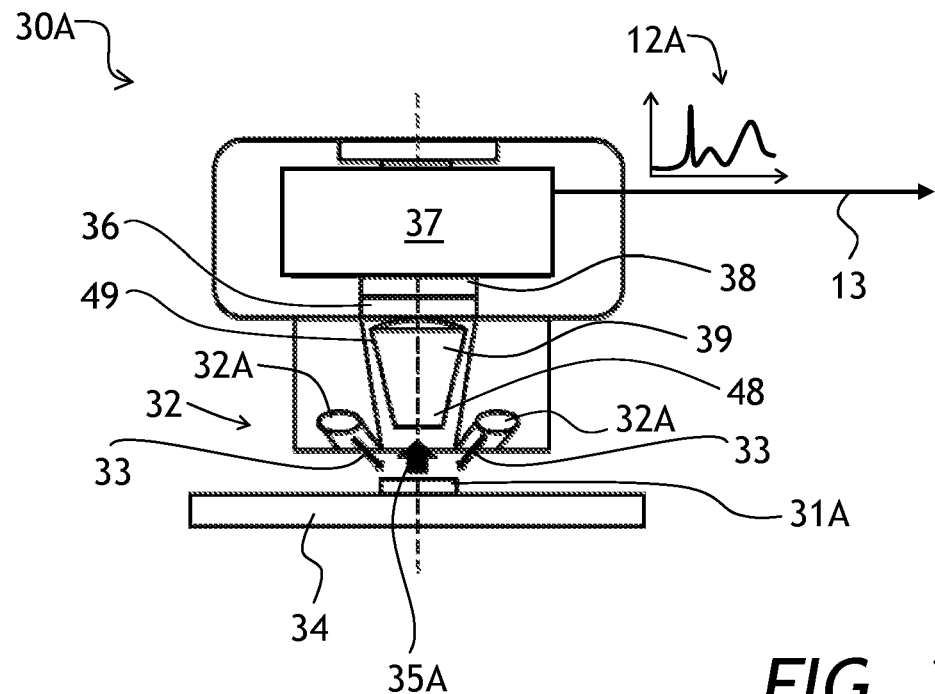
FIGS. 3A, 3B, and 3C are side cross-sectional views of a compact spectrometer configured for operation in diffuse reflection, transmission, and transflection, respectively, for use in the medication assurance system of FIG. 1.

Turning now to FIG. 3A with further reference to FIG. 1, a preferred embodiment 30A (FIG. 3A) of the portable NIR reflection spectrometer 12 (FIG. 1) is shown. The portable NIR reflection spectrometer 30A of FIG. 3A includes a light source 32 for illuminating a medication 31A e.g. the pill 11, and a medication holder 34 for holding the medication 31A being illuminated by the light source 32. The light source 32 is configured for directing light 33 at the medication holder 34 at an acute angle as shown. An LVF 36 receives light 35A diffusely reflected from the medication 31A. A photodetector array 38 is optically coupled to the LVF 36 for wavelength-selective detection of the diffusely reflected light 35A. An on-board microcontroller 37 controls the operation of the light source 32 and processes the data from the photodetector array 38, thus obtaining the spectrum 12A of the diffusely reflected light 35A.

The portable NIR reflection spectrometer 30A preferably includes a light collecting element 39 disposed between the medication holder 34 and the LVF 36, for collecting the diffusely reflected light 35A from the medication 31A when the medication 31A is placed into the medication holder 34 and illuminated by the light source 32, and coupling the diffusely reflected light 35A to the LVF 36. In the embodiment shown, the light collecting element 39 is a tapered light pipe having a narrower end 48 for receiving the diffusely reflected light 35A, and a broader end 49 near the LVF 36 for mixing and spreading the received diffusely reflected light 35A, with an optional lens element on the broader end 49 facing the LVF 36. Furthermore, in the preferred embodiment shown in FIG. 3A, the light source 32 includes first and second incandescent light bulbs 32A disposed symmetrically on both sides of the light collecting element 39 for symmetrically illuminating the medication 31A placed in the medication holder 34. Advantageously, the first and second incandescent light bulbs 32A provide a smooth and wide infrared spectrum of the illuminating light 33. A more detailed description of the portable NIR reflection spectrometer 30A is provided in a co-pending U.S. patent application Ser. No. 14/079,280, which is incorporated herein by reference.

Figure 3B:
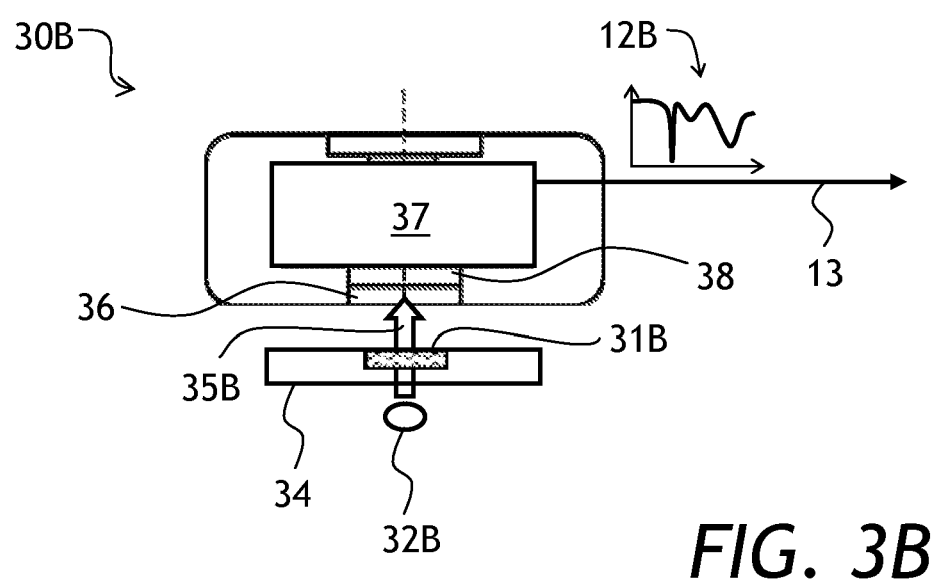

Referring to FIG. 3B with further reference to FIGS. 1 and 3A, a transmission portable spectrometer 30B (FIG. 3B) can be used in place of the portable NIR reflection spectrometer 12 (FIG. 1). The portable NIR transmission spectrometer 30B of FIG. 3B is similar to the portable NIR reflection spectrometer 30A of FIG. 3A, only a single light source, that is, an incandescent lamp 32B, is placed under the sample holder 34 holding a transparent e.g. liquid medication 31B. In other words, the liquid medication 31B is placed between the light source, that is, the incandescent lamp 32B, and the LVF 36. The incandescent lamp 32B provides a beam of light 35B, which propagates through the liquid medication 31B. The on-board microcontroller 37 controls the operation of the incandescent lamp 32B and processes the data from the photodetector array 38 to obtain a transmission spectrum 12B of the liquid medication 31B. Preferably, the portable spectrometers 30A and 30B of FIGS. 3A and 3B, respectively, operate in the near-infrared (NIR) spectral range of 800 nm to 2500 nm, where inexpensive photodetector arrays can be used.

Figure 3C:
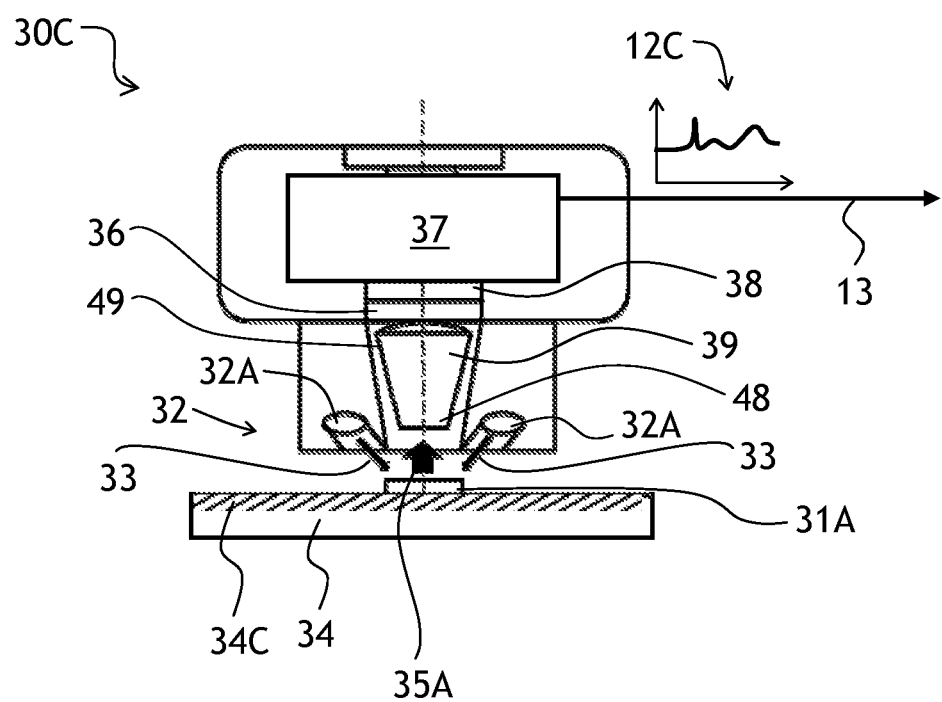

Turning to FIG. 3C with further reference to FIGS. 1, 3A, and 3B, a transflection portable spectrometer 30C (FIG. 3C) can be used in place of the portable NIR reflection spectrometer 12 (FIG. 1). The portable NIR transflection spectrometer 30C of FIG. 3C is similar to the portable NIR reflection spectrometer 30A of FIG. 3A. In the portable NIR transflection spectrometer 30C of FIG. 3C, the medication holder 34 is coated with a reflective coating 34C. In operation, the illuminating light 33 is not only reflected from the medication 31A, but is also transmitted through the medication 31A, reflected from the reflective coating 34C, is transmitted again through the medication 31A in an opposite direction, and is collected by the light collecting element 39. The light reflected from the reflective coating 34C can be reflected by a lower side of the medication 31A, reflected again by the reflective coating 34C, and is transmitted through the medication 31A for collection by the light collecting element 39. In other words, the presence of the reflective coating 34C allows one to obtain a combination of diffuse reflection and transmission spectrum, herein termed "transflection spectrum" 12C of the medication 31A. The transflection measurement may be beneficial for translucent or powdered medications 31A.

Figure 4A:
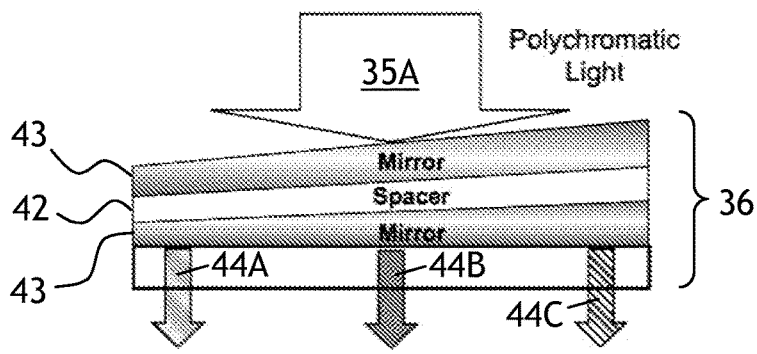
FIG. 4A is a side cross-sectional view of an LVF usable in the spectrometers of FIGS. 3A and 3B.
Figure 4B:
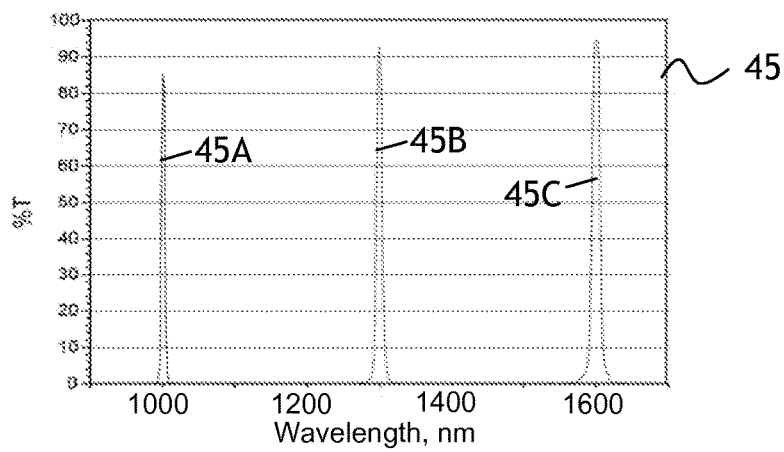
FIG. 4B is a transmission spectrum of the LVF of FIG. 4A at different locations on the LVF.

Turning to FIGS. 4A and 4B, the operation of the LVF 36 of the portable spectrometers 30A and 30B of FIGS. 3A and 3B, respectively, is considered in more detail. In FIG. 4A, the LVF 36 is flipped upside down as compared to FIGS. 3A and 3B, so that the reflected light 35A propagates downwards, not upwards as in FIGS. 3A and 3B. The LVF 36 of FIG. 4A includes a wedged spacer 42 sandwiched between wedged dichroic mirrors 43, to form a Fabry-Perot cavity with a laterally variable spacing between the dichroic mirrors 43. The wedge shape of the LVF 36 makes its transmission wavelength laterally variable, as shown with arrows 44A, 44B, and 44C pointing to individual transmission peaks 45A, 45B, and 45C, respectively, of a transmission spectrum 45 (FIG. 4B) shown under the LVF 36. In operation, the diffusely reflected light 35A impinges on the LVF 36, which separates the diffusely reflected light 35A into the individual spectral components shown with the arrows 44A to 44C.

Figure 5:
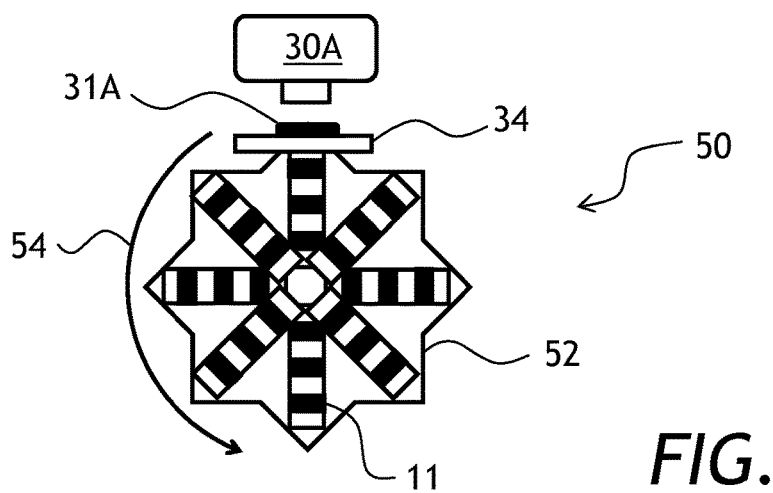
FIG. 5 is a schematic view of a pill dispenser of the invention.

Referring now to FIG. 5, the portable diffuse NIR reflection spectrometer 30A can be coupled to an automatic medication dispenser 50 for automatically dispensing the medication 31A the times of required administering of the medication 31A to the subject. In the embodiment shown, the automatic medication dispenser 50 includes a cartwheel 52 loaded with the pills 11 and rotatable as shown by an arrow 54. The medication dispenser 50 can be mechanically coupled to the medication holder 34 to place the medication 31A on the medication holder for spectral authentication as explained above. Of course, the automatic medication dispenser 50 can also be used with the spectrometer 12 of FIG. 1, as well as with other spectrometer types, such as the portable NIR transmission spectrometer 30B of FIG. 3B.

Still referring to FIG. 5, the embodiment of the medication assurance system 10 having the automatic medication dispenser 50 is particularly beneficial in clinical trials, in which some of the subjects are given new drugs being tested and some are given empty tablets called placebos. The automatic medication dispenser 50 of the medication assurance system 10 can be programmed so that the medical personnel servicing a clinical trial is unaware of who of the participating human subjects is given the new drug and who is given the placebos, thus enhancing reliability and fidelity of the trial.

Figure 6:
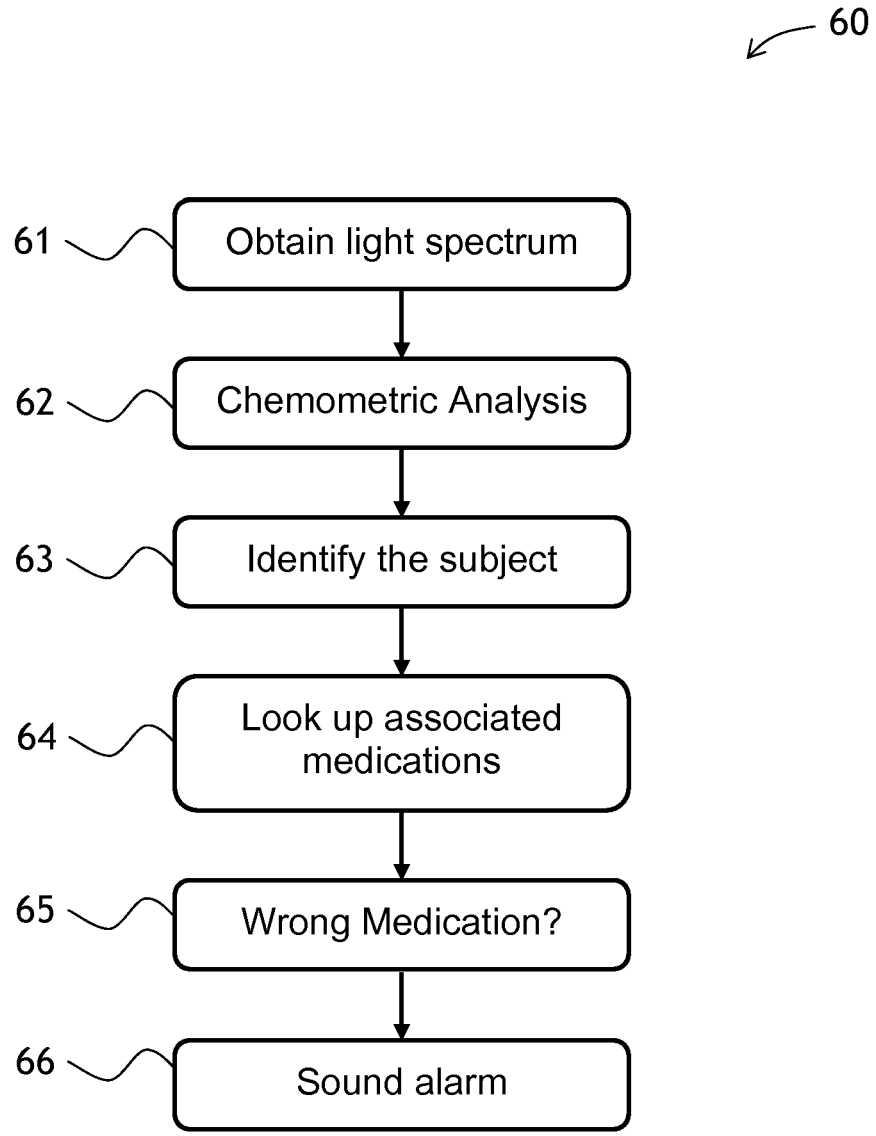
FIG. 6 is a flow chart of a method of the invention for preventing a subject from taking an incorrect medication.

Turning to FIG. 6 with further reference to FIGS. 1, 3A, and FIG. 3B, a method 60 for preventing a subject from taking an incorrect medication can be practiced using the medication assurance system 10 of FIG. 1. The method 60 of FIG. 6 includes a step 61 of using a portable spectrometer, such as the diffuse reflection spectrometer 12 of FIG. 1, the diffuse reflection spectrometer 30A of FIG. 3A, or a transmission spectrometer 30B of FIG. 3B, to obtain a light spectrum of a medication. The light spectrum can include the diffuse reflection spectrum 12A (FIG. 3A), the transmission spectrum 12B (FIG. 3B), or a transflection spectrum 12C (FIG. 3C). In a step 62, the medication (the pill 11 of FIG. 1, the medication 31A of FIG. 3A, or the transparent medication 31B of FIG. 3B) is identified by performing a chemometric analysis of the light spectrum obtained in the previous step 61. The chemometric analysis can include Principal Component Analysis (PCA) followed by Soft Independent Modeling of Class Analogy (SIMCA). The chemometric analysis can also include Support Vector Classification (SVC) or Support Vector Regression (SVR); Linear Discriminant Analysis (LDA) or Quadratic Discriminant Analysis (QDA); TreeBagger Analysis or Random Forest Analysis; Partial Least Square Discriminant Analysis (PLS-DA); and other data regression and multivariate analysis methods known to the skilled person.

In a step 63, the subject is identified using an identification or biometric device, such as the fingerprint scanner 14. In a step 64, the controller 16 of the medical assurance system 10 consults a pre-existing record e.g. a table including the subject, or patient, identified in the previous step 63, to determine a medication the identified subject should take, that is, the medication associated with the identified subject. In a step 65, the medication identified in the second step 62 is compared with the associated medication. If it is not the associated medication, then in a step 66, an audio and/or visual alarm is generated for informing the subject that the medication 11, 31A, or 31B, as the case may be, is an incorrect medication and should not be taken by the subject (patient). Furthermore, a blocking mechanism can be provided to physically prevent the subject from taking the "wrong" medication. The blocking mechanism, not shown, can be coupled to the controller 16 of FIG. 1, to enable the controller to physically block the medication 11 once the incorrect medication has been identified as such. The blocking mechanism can be integrated into the medication holder 34 of FIGS. 3A to 3C.

Figure 7:
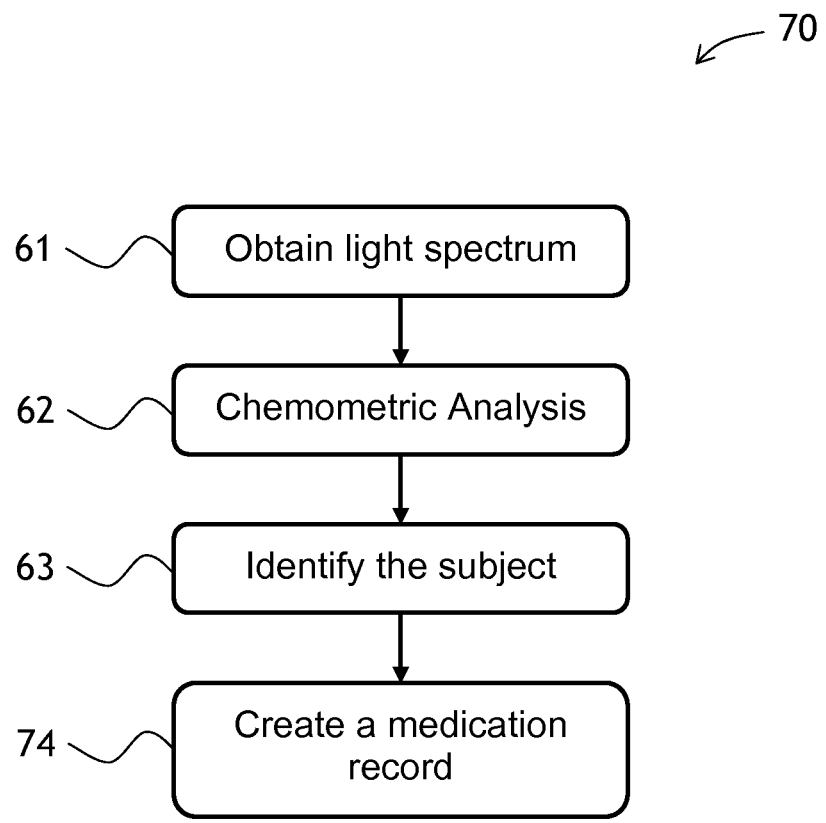
FIG. 7 is a flow chart of a method of the invention for tracking administering of a mediation to a subject.

Referring now to FIG. 7 with further reference to FIG. 1, the first three steps 61 to 63 of a method 70 for tracking administering of a mediation to a subject are the same as the first three steps 61 to 63 of the method 60 of FIG. 6. The method 70 of FIG. 7 further includes a fourth step 74 of creating a record including: a timestamp; the medication identified in the chemometric analysis step 62; and the subject identified the subject identification analysis step 63. The record created in the step 74 can form a part of medication history of a patient, or form a part of an objective experimental base of a clinical trial.

In preferred embodiments of the methods 60 and 70 of FIGS. 6 and 7, respectively, the portable diffuse reflection spectrometer 31A of FIG. 3A is used in the measurement steps 61, to obtain the diffuse reflection spectrum 12A. Utilization of the laterally variable filter 36 optically coupled to the photodetector array 38 results in a very compact spectrometer weighting less than 100 g. Due to effective light utilization and the ability to measure absorption at all wavelength simultaneously (i.e. no scanning, no single wavelength measurement) by the spectrometer 31A, the data collection time can be very small, e.g. less than 1 second.

The performance of the portable diffuse reflection spectrometer 31A of FIG. 3A in drug identification has been verified experimentally. Tests have been performed to determine a degree of certainty with which different medications can be identified and distinguished from each other. The tests described below differentiate between "generic" and "illegal" versions of similar drugs, establishing a proof that NIR diffuse reflection spectroscopy can indeed be used to identify drugs.

A MicroNIR™ diffuse reflection miniature spectrometer manufactured by JDS Uniphase Corporation, Milpitas, Calif., USA, was used to collect the spectral data. The MicroNIR spectrometer weights only 60 g and measures 45 mm×42 mm. Prior to the samples analysis, the MicroNIR wavelength scale was verified using a U.S. Pharmacopeia (USP) NIR wavelength standard (Lot F0G007, Catalogue number 1457844). The NIR spectrometer was zeroed (0% reflectance) using a 2% reflective dark reference from Lab-Sphere, New Hampshire, USA, and a 100% baseline achieved by measuring a 99% reflective Spectralon™ ceramic reference (LabSphere). This sequence of re-zeroing and baseline acquisition was repeated once every 15 minutes during sample analysis periods. All samples were measured either through glass vials (capsule blend/powder) or "as is" (tablets).

Three tablets were measured for each sample brand. To minimize stray light and baseline offset differences, tablets of a same brand were scanned in exactly the same orientation. Each of the three tablets was then measured once, with the brand owner logo face down, that is, towards the photodetector array 38, and strength numeration face up, that is, away from the photodetector array 38. Sixty (60) scans were taken per sample spectrum, using an integration time of 5600 microseconds. Each spectrum to be analyzed was the mean of 60 scans in the wavelength range 880 nm-1668 nm at 6 nm intervals.

For different drug comparisons, second derivative absorbance (Savitsky-Golay smoothing method, 11 data points smoothed) was achieved exporting the MicroNIR's reflectance data into the Unscrambler GENX software v. 10.1. First, a reflectance was transposed into absorbance, and then a spectral second derivative transformation of this absorbance data was performed for a wavelength range of 905 nm to 1637 nm.

Figure 8:
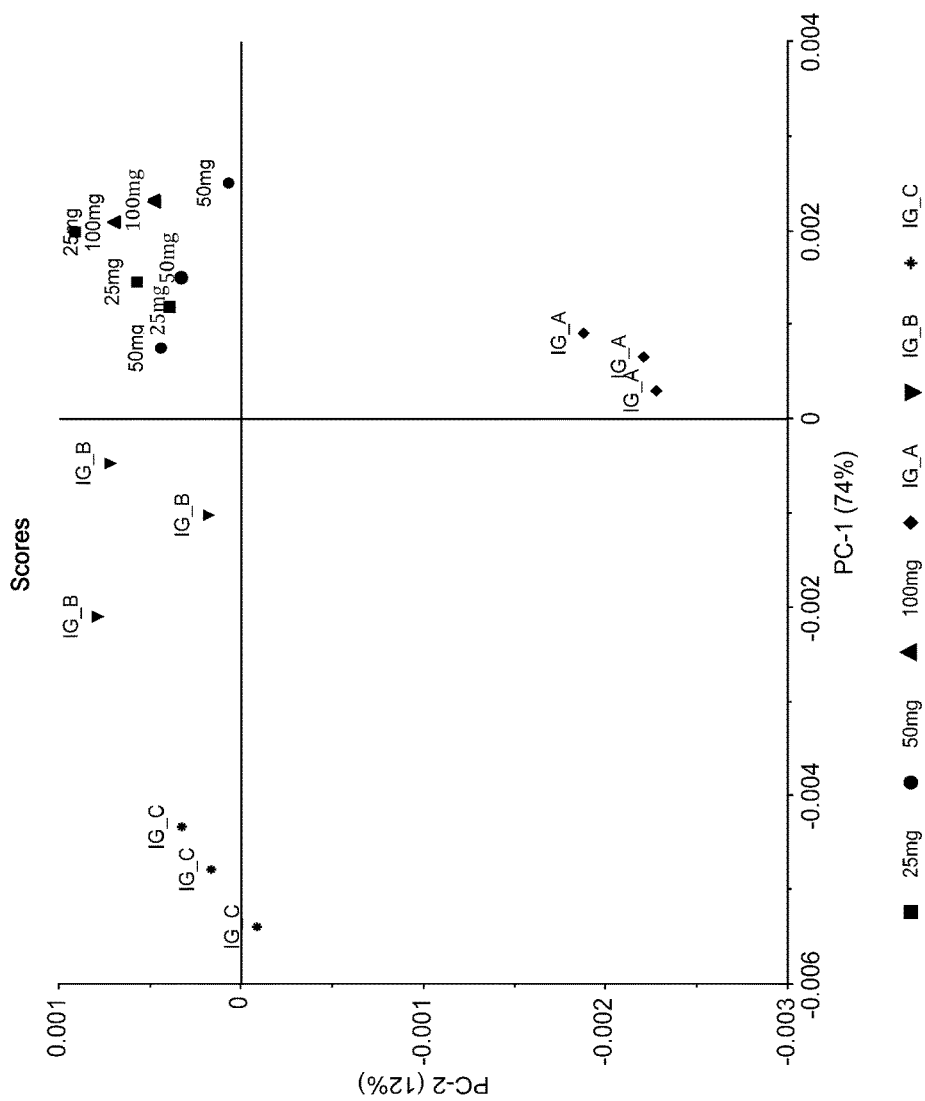
FIG. 8 is a two-dimensional Principle Component Analysis (PCA) scores plot for Sildenafil™ drug of different strengths and Kamagra™, Zenegra™, and Sildigra™ XL illegal generic substitutions.

To distinguish between various drug types, the second derivative absorbance data were imported into software for generation of PCA. The chemometric software used was Unscrambler GENX v. 10.2 developed by Camo A/S Software, Norway. PCA was performed on the second derivative absorbance data from each authentic Viagra® strength (25 mg, 50 mg and 100 mg Sildenafil) and the illegal generic Kamagra® 100 mg ("IG_A"), Zenegra® 100 mg ("IG_B") and Sildigra® XL 150 mg ("IG_C") tablets. In FIG. 8, the PCA scores plot is shown for each authentic Sildenafil strength and illegal generic drug variants. The horizontal PC-1 and vertical PC-2 axes correspond to two latent variables termed "principal components", accounting together for 86% of the total spectral information contained in the calibration library or primary reference data. One can see that Viagra tablets are clearly distinguishable from the illegal generic versions of the drug.

Figure 9:
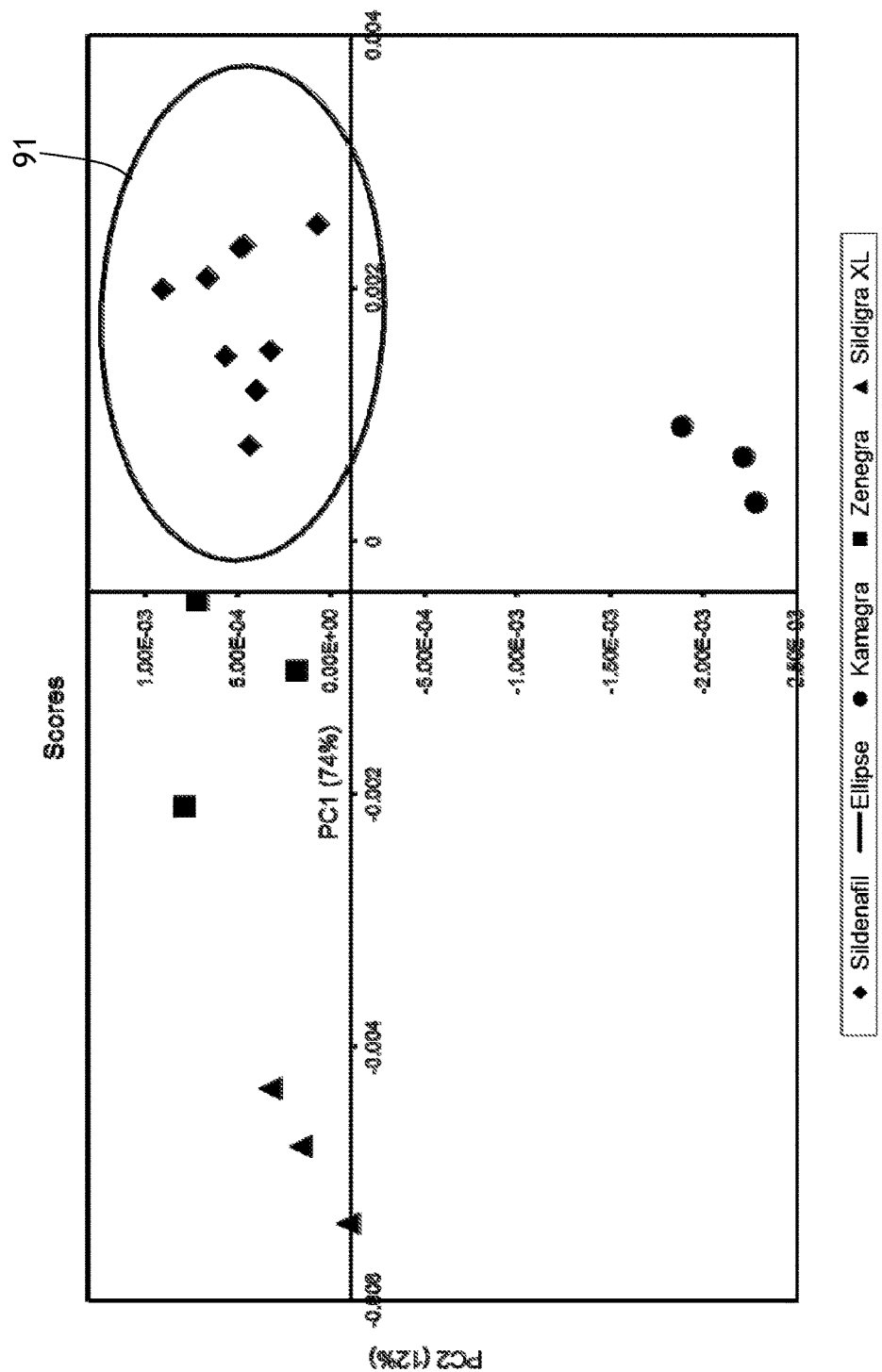
FIG. 9 is a two-dimensional PCA scores plot for Sildenafil, Kamagra, Zenegra, and Sildigra XL tablets, showing a 95% equal frequency ellipse for Sildenafil.

Referring to FIG. 9, the data of FIG. 8 is delineated with a 95% equal frequency ellipse 91 drawn around the authentic Viagra tablets signs shown in diamonds, in which all strengths have been grouped together. The scores points for the Kamagra 100 mg are shown with circles; Zenegra 100 mg are shown with squares; and Sildigra XL 150 mg are shown with triangles. Any individual tablet(s), illegal generic or otherwise, that fall outside the 95% equal frequency ellipse 91, are highly unlikely to come from a same source. The authentic tablets (diamonds in FIG. 9) were discriminated from the illegal generic types (circles, squares, and triangles in FIG. 9), with Zenegra 100 mg being most similar in NIR spectra, and therefore similar in its organic composition to the Pfizer product. In other words, Zenegra 100 mg is likely to contain similar active and excipient materials. Kamagra was discriminated from all other products along the second (vertical) axis PC2.

Figure 10:
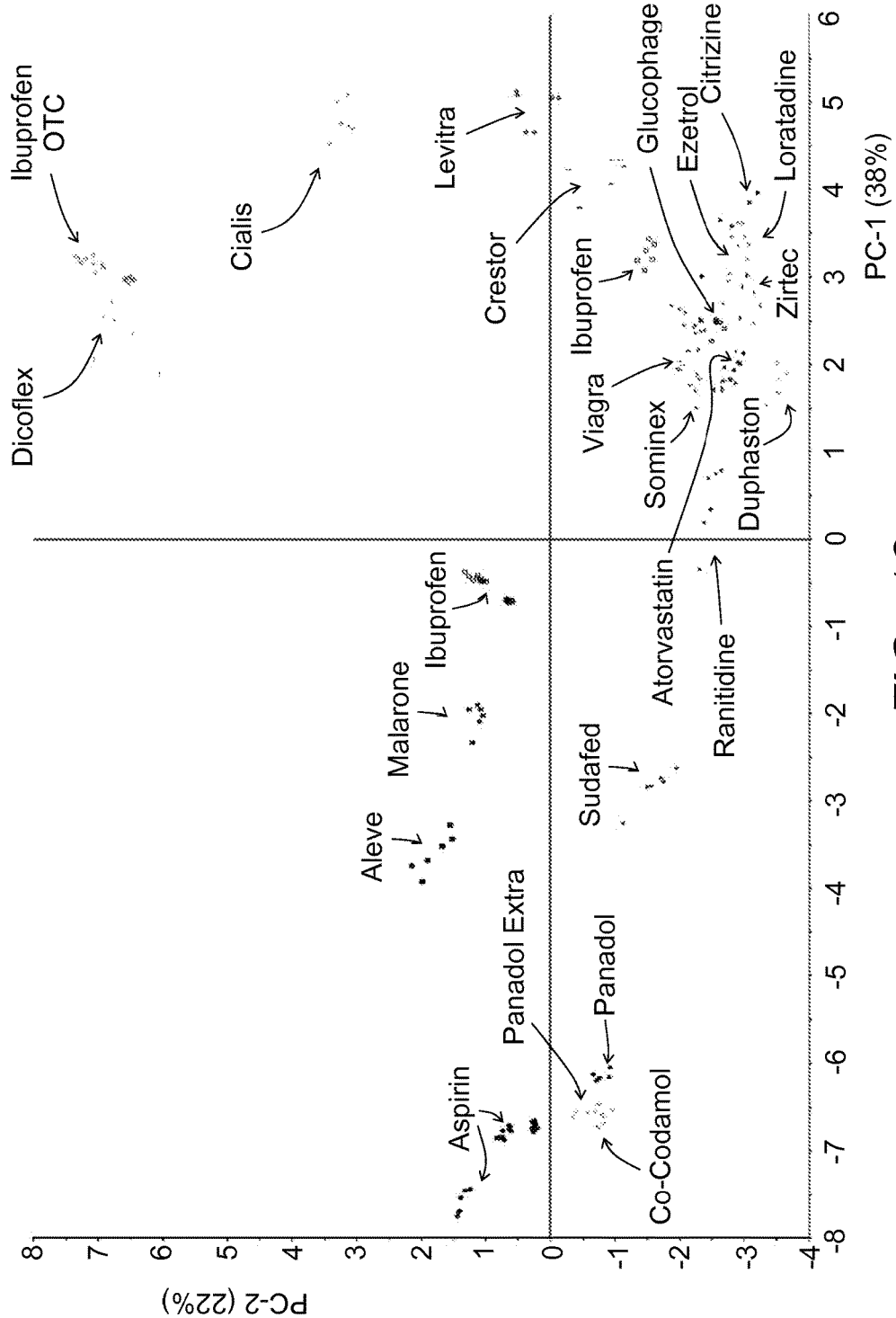
FIG. 10 is a two-dimensional PCA scores plot for twenty three various drugs tested by the reflective compact spectrometer of FIG. 3A.
Figure 11:
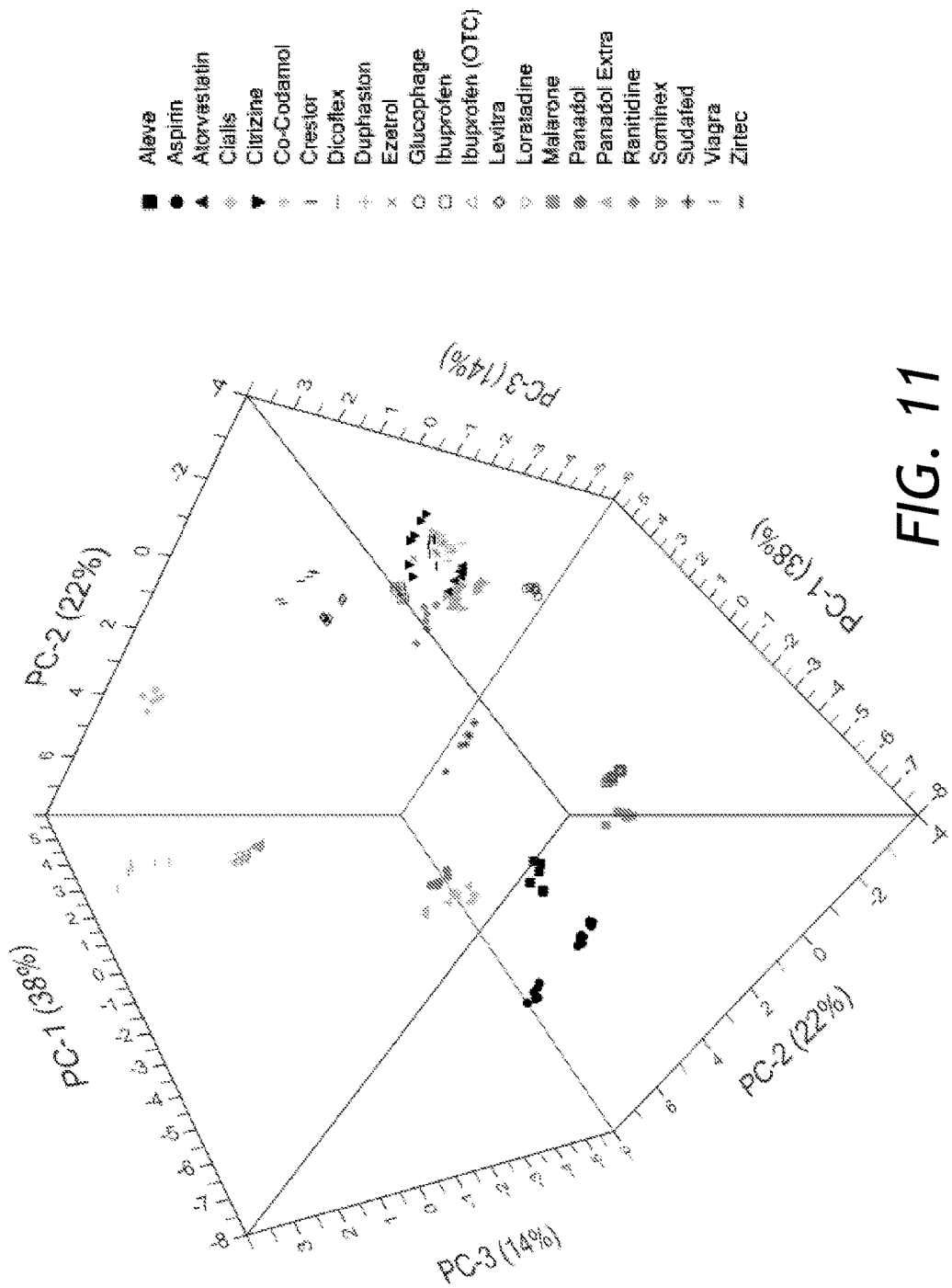
FIG. 11 is a three-dimensional PCA scores plot for the drugs shown in FIG. 10.

Turning to FIG. 10, a two-dimensional PCA scores plot is shown for twenty three different drugs measured using the reflective spectrometer 30A of FIG. 3A, including Aleve®, Aspirin, Alorvastatin®, Cialis®, Citrizene®, Co-Codamol®, Crestor®, Dicoflex®, Duphaston®, Ezetrol®, Glucophage®, Ibuprofen®, Ibuprofen (OTC), Levitra®, Loratadine®, Malarone®, Panadol®, Panadol Extra, Ranitidine®, Sominex®, Sudafed®, Viagra, and Zirtec®. The PCA scores plot is shown in two axes: PC-1 (38%), and PC-2 (22%). Referring now to FIG. 11, a three-dimensional PCA scores plot is shown for the above twenty three drugs, in three axes: PC-1 (38%), PC-2 (22%), and PC-3 (14%).

The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A spectrometer comprising:
    a laterally variable filter to receive light reflected from a medication; and
    a photodetector array to obtain data based on the reflected light,
        where
            at least some of the light is received at a bottom portion of the medication, and
            the medication and medication use information are identified based on a chemometric analysis of the data.

2. The spectrometer of claim 1, further comprising:
    a light collecting element to couple the light to the laterally variable filter.

3. The spectrometer of claim 2,
    where the light collecting element is a tapered light pipe, and
    where the tapered light pipe comprises:
        a narrower end to receive the light, and
        a broader end to mix and spread the light.

4. The spectrometer of claim 1, where the medication is illuminated by a light source that is under the medication.

5. The spectrometer of claim 1, where the medication is illuminated by two light sources that are disposed on both sides of the medication.

6. The spectrometer of claim 1, where the spectrometer operates in a near-infrared (NIR) spectral range of 800 nm to 2500 nm.

7. The spectrometer of claim 1,
    where the data is transmitted to a controller, and
    where the controller identifies the medication and the medication use information based on the chemometric analysis of the data.

8. The spectrometer of claim 1, where a controller determines that the medication is not to be taken by a subject based on identifying the medication and the medication use information.

9. A method comprising:
    receiving, by using a laterally variable filter, light reflected from a medication,
        where at least some of the light is received at a bottom portion of the medication; and
    obtaining, by using a photodetector array, data based on the reflected light, where the medication and medication use information are identified based on a chemometric analysis of the data.

10. The method of claim 9, where the data is a combination of diffuse reflection and transmission spectrum.

11. The method of claim 9, where a controller determines that the medication is not to be taken by a subject based on identifying the medication and the medication use information.

12. The method of claim 11, where the subject is identified by using a biometric device.

13. The method of claim 11, where the subject is physically blocked from taking the medication based on determining that the medication is not to be taken by the subject.

14. The method of claim 9, further comprising:
creating a record based on identifying the medication; and
transmitting the record to a centralized storage of records from multiple medical assurance systems.

15. The method of claim 9, further comprising:
using a light source to illuminate the bottom portion of the medication before the light is reflected from the medication.

16. A spectrometer comprising:
a light collecting element to:
 receive light reflected from a medication, and
 mix and provide the light,
a laterally variable filter to receive the light from the light collecting element; and
a photodetector array to obtain data based on the light received by the laterally variable filter,
 where the medication is identified by performing a chemometric analysis of the data.

17. The spectrometer of claim 16,
where a medication holder holds the medication, and
where the light collecting element is disposed between the medication holder and the laterally variable filter.

18. The spectrometer of claim 16, where the laterally variable filter comprises a wedged spacer between dichroic mirrors.

19. The spectrometer of claim 16,
where the light collecting element is a tapered light pipe, and
where the tapered light pipe comprises:
 a narrower end to receive the light, and
 a broader end to mix and spread the light.

20. The spectrometer of claim 19,
where the tapered light pipe further comprises a lens element on the broader end, and
where the broader end faces the laterally variable filter.

* * * * *